United States Patent
Don Michael et al.

[11] Patent Number: 5,971,936
[45] Date of Patent: Oct. 26, 1999

[54] METHOD AND APPARATUS FOR REPRODUCING HEART SOUNDS

[76] Inventors: T Anthony Don Michael; Nirendra G. A. Abeyesundere, both of 4109 Sill Pl., Bakersfield, Calif. 93306; Darrel C Perera, 3312 A Horion Pl., Colombo, Sri Lanka

[21] Appl. No.: 09/040,439

[22] Filed: Mar. 18, 1998

[51] Int. Cl.⁶ .............................. A61B 5/02; A61B 7/04
[52] U.S. Cl. ........................................... 600/528; 381/67
[58] Field of Search .............................. 600/528; 381/67; 181/131

[56] References Cited

U.S. PATENT DOCUMENTS

| | | |
|---|---|---|
| 4,170,717 | 10/1979 | Walshe . |
| 4,254,302 | 3/1981 | Walshe . |
| 4,424,815 | 1/1984 | Kuntz . |
| 4,528,689 | 7/1985 | Katz ........................................ 381/67 |
| 4,598,417 | 7/1986 | Deno . |
| 4,618,986 | 10/1986 | Hower . |
| 4,720,866 | 1/1988 | Elias et al. . |
| 4,770,189 | 9/1988 | Shyu . |
| 4,783,813 | 11/1988 | Kempka . |
| 4,783,814 | 11/1988 | Foley . |
| 4,792,145 | 12/1988 | Eisenberg et al. . |
| 4,932,880 | 6/1990 | Kotick et al. . |
| 4,991,581 | 2/1991 | Andries .................................... 600/528 |
| 5,010,889 | 4/1991 | Bredesen et al. . |
| 5,025,809 | 6/1991 | Johnson et al. ........................ 600/528 |
| 5,165,417 | 11/1992 | Murphy, Jr. . |
| 5,218,969 | 6/1993 | Bredesen et al. . |
| 5,285,499 | 2/1994 | Shannon et al. . |
| 5,347,583 | 9/1994 | Dieken et al. . |
| 5,497,426 | 3/1996 | Jay . |
| 5,557,681 | 9/1996 | Thomasson . |

*Primary Examiner*—William E. Kamm
*Assistant Examiner*—Carl H. Layno
*Attorney, Agent, or Firm*—Pillsbury Madison & Sutro

[57] ABSTRACT

A method and apparatus for audibly reproducing a heartbeat at a user selected repetition rate by the steps of: detecting heart sound patterns and storing a representation of heart sound patterns having a duration that encompasses one heartbeat; analyzing the stored representation to determine the duration of one heartbeat; audibly and repeatedly reproducing a portion of the stored representation extending over a period equal to the duration of one heartbeat such that each repetition of the audibly reproduced portion extends over a time period substantially equal to the duration of one heartbeat; and selecting the repetition rate at which the portion of the stored representation is repetitively produced.

11 Claims, 3 Drawing Sheets

METHOD AND APPARATUS FOR REPRODUCING HEART SOUNDS

BACKGROUND OF THE INVENTION

The present invention relates to a method and apparatus for reproducing the audible sound produced by a heartbeat in order to facilitate the diagnosis of coronary diseases and abnormalities and to aid in teaching such diagnoses.

A heartbeat is a single complete pulsation of the heart, consisting of a complete cardiac contraction-relaxation sequence, and produces an audible sound pattern. Contraction is represented by the first sound $S_1$, the beginning of relaxation by the second sound $S_2$. In addition, sounds may take any one of a number of different forms based on the duration and the relationship to $S_1S_2$. The audible sound pattern produced by a single heartbeat may be classified as heart sounds, or heart murmurs, or a combination of a heart sound and a heart murmur. A heart murmur is a protracted sound usually over 40 msec which may occur in systole during cardiac contraction or in diastole during cardiac relaxation. A heart sound is a nonprotracted sound and a murmur is a protracted sound. Either a heart sound or a murmur may take one of a number of specific forms. Depending on its specific form, a heart sound may be indicative of a normal, healthy, heart, or an abnormal or diseased heart. A diastolic murmur is usually abnormal. Diastolic murmurs are heard between the second and first sounds.

Hereinafter, the term "heartbeat" will be understood to refer to either a heart sound, or a murmur, or a combination thereof; the sounds produced by one heartbeat will be referred to as an audible sound pattern, or sound pattern; and sounds produced by a plurality of successive heartbeats will be referred to as audible sound patterns, or sound patterns.

Interpretation of the audible sound pattern produced by a heartbeat, or more generally the audible sound patterns produced by a succession of heartbeats, is known as auscultation and represents one of the oldest, and most effective, techniques used in the practice of medicine. A skilled and experienced physician can obtain critical information about the condition of a patient's heart from proper interpretation of such audible sound patterns.

However, auscultation is inherently a demanding art and is rendered more difficult by the fact that an irregularity and/or the relatively high repetition rate of heartbeats interferes with the mental processes involved in such interpretation.

Specifically, heartbeats produce repetitive audible sound patterns which are substantially identical from one heartbeat to the next. Because of the rate at which successive heartbeats normally recur, it has been found that after a physician has heard one heartbeat, and is attempting to interpret it, the next heartbeat occurs and interferes with the interpretation process.

It has been proposed to facilitate diagnosis by recording the audible sound patterns produced by a succession of heartbeats in auscultable grouped units (see Det) and then playing back the recording at a reduced rate, or speed, to facilitate interpreting the grouped sounds. Normally, this procedure has a significant drawback in that it reduces the frequency components of all of the recorded heartbeat, with the result that the heartbeats which are reproduced for diagnosis differ significantly from the actual heartbeats which physicians have been trained to interpret (defined as auscultable sounds).

BRIEF SUMMARY OF THE INVENTION

It is an object of the present invention to provide a method and apparatus which allow audible sound patterns produced by heartbeats to be interpreted by a physician in a substantially improved manner.

Another object of the invention is to allow one sound pattern to be faithfully reproduced at an arbitrarily selected repetition rate without altering the frequency components or relative loudness of each portion thereof.

The above and other objects are achieved, according to the present invention, by a method for audibly reproducing the sound pattern of a heartbeat at a user-selected repetition rate, the method comprising: detecting sound patterns produced by successive heartbeat and storing a representation of the sound patterns over a time period that encompasses at least one heartbeat cycle; analyzing the stored representation to determine the duration of one heartbeat cycle; audibly reproducing a portion of the stored representation extending over one heartbeat cycle such that the audibly reproduced portion extends over a time period substantially equal to the duration of one heartbeat cycle; and repeating the step of audibly reproducing at the user-selected repetition rate, which repetition rate is lower than the heartbeat rate of the heartbeats whose sound patterns are detected. A heartbeat corresponds to a single complete pulsation of the heart and the resulting sound pattern is normally recognized by auscultation with a stethoscope.

Objects according to the invention are further achieved by the provision of apparatus for audibly reproducing the sound pattern produced by a heartbeat at a user-selected repetition rate, the system comprising: means for detecting the audible sound patterns produced by heartbeats and storing a representation of such sound patterns occurring over a period of time that encompasses one heartbeat cycle; means for analyzing the stored representation to determine the duration of one heartbeat cycle; means for audibly and repeatedly reproducing a portion of the stored representation extending over one heartbeat cycle such that each repetition of the audibly reproduced portion extends over a time period substantially equal to the duration of one heartbeat cycle; and means for selecting the repetition rate at which the portion of the stored representation is repeatedly produced.

DETAILED DESCRIPTION OF THE INVENTION

In the first step of a method according to the invention, the audible sound patterns produced by heartbeats are detected over a period of time which is sufficiently long to encompass at least several heartbeats. For individuals who are not experiencing a medical emergency, the time period need not be longer than 2 seconds. Each heartbeat has a characteristic sound pattern which can be represented phonetically by one or a series of syllables or phonemes. Successive heartbeats normally produce substantially identical sound patterns.

Before the sound pattern representing one heartbeat can be reproduced, or played back, at a desired repetition rate, the beginning and end of such a pattern must be isolated from the detected signal. According to the invention, this can be achieved in the manner to be described below.

In a first step, detected audible sound patterns are sampled at a suitable rate and each sample is converted into a multibit binary word, or value. To allow correct recognition and interpretation of the heart sound produced by a heartbeat, the detected signal should contain frequency components up to 1 kHz. To this end, a sampling frequency of 4 kHz is preferred, even though 2 kHz would theoretically suffice. According to an exemplary embodiment of a system according to the invention, the digital word representing the amplitude of each sample consists of twelve bits, including a sign bit and eleven data bits that can represent amplitude values, in decimal form, from −2047 to +2047.

Initially, sound patterns are sampled during a period of several seconds while the user listens to the sounds to verify that the signal being recorded is of good quality.

The binary values representing successive samples are stored in a memory at successive memory addresses in an order corresponding to the time order of the signal samples. Each address may correspond to one or more memory locations, depending on the architecture of the memory.

Figure 1:
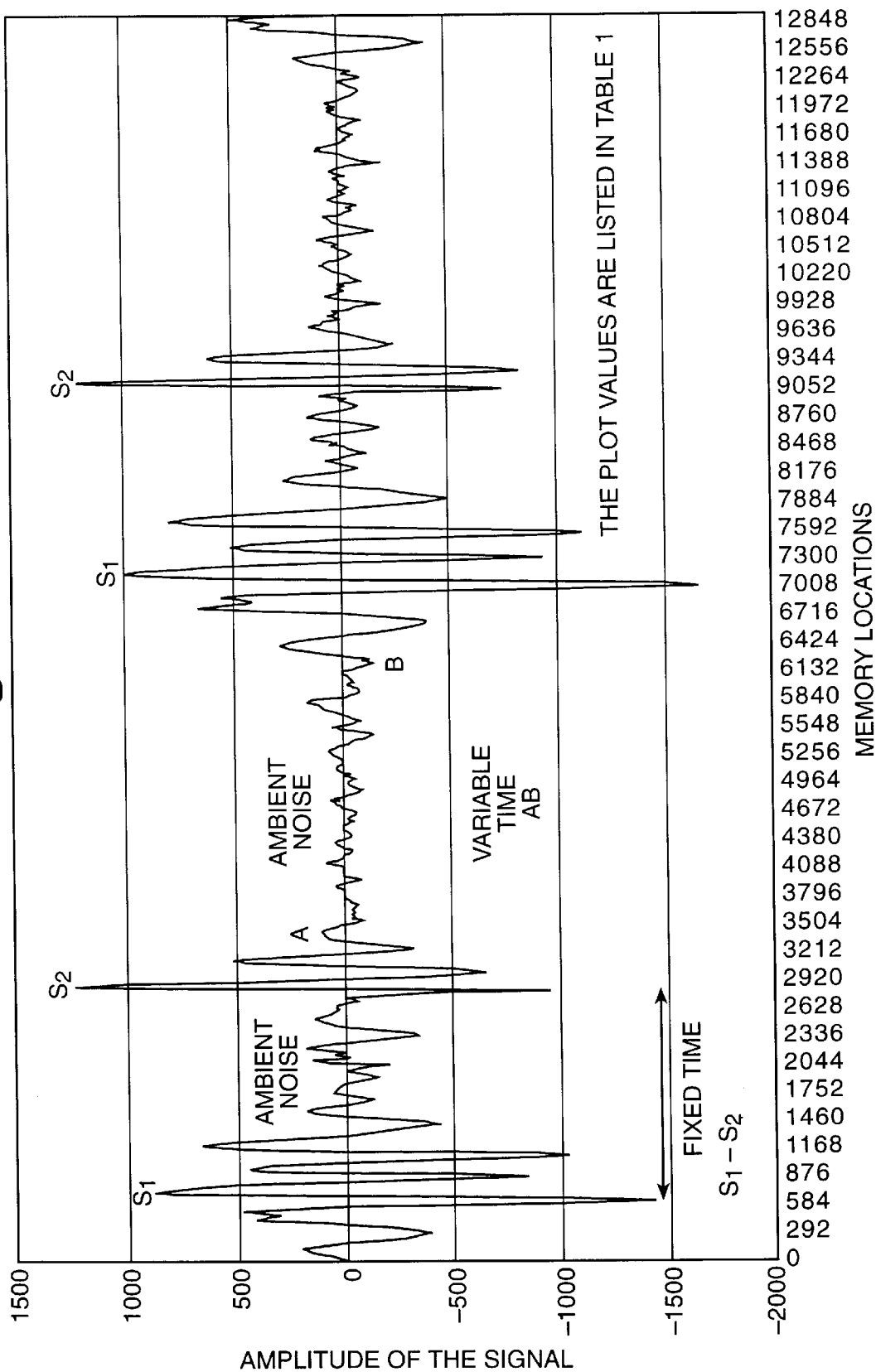
FIGS. 1 and 2 are waveform diagrams illustrating recorded audible sound patterns over a period of approximately two successive heartbeats.

FIG. 1 shows an exemplary sound pattern signal, constituting the output of a stethoscope microphone, over a period of approximately 1.6 seconds. The abscissa of FIG. 1 identifies the memory locations where successive samples are stored, while the ordinate represents the stored sample values in decimal units.

In the illustrated example, each sample is stored at a memory address designating two successive memory locations. Thus, 12,876 memory locations are associated with 6,438 addresses. At a sampling rate of 4 kHz, the samples stored at these addresses are based on a signal having a duration of 1.6095 seconds (6438/4000).

As the next step in the process of isolating the samples representing one heartbeat, the stored values are analyzed to divide the samples into groups, each group being referred to hereinafter as a subcycle unit. Each subcycle unit represents a respective half cycle of variation of sound pattern. In addition, each of sample values of zero at two or more consecutive addresses will be treated as a subcycle unit.

This analysis involves first identifying each memory address which stores a value equal to zero, but is bordered by memory addresses storing finite values with respectively different polarities, or signs. In more general terms, a memory address which is bordered by memory addresses storing values having respectively different algebraic signs can be treated as a memory address associated with a zero crossing of the sound pattern signal.

Once the memory addresses associated with zero signal crossings have been identified, the memory addresses can be grouped into subcycle units. A subcycle unit consists of successive samples having finite values and bounded by zero crossings. With respect to the signal shown in FIGS. 1 and 2, the grouping of memory locations into such subcycle units is shown below as Table 1. Table 1 shows the range of memory locations, peak value and duration of each subcycle unit and represents the structure of a database storing the illustrated data.

TABLE 1

Analysis to determine the number of syllables & duration

| Sub Cycle Count | From Mem Loc | To Mem Loc | Peak Value | Duration | Above Threshold 1st pass | Above Threshold 2nd pass | Total Duration | No. of Sub cycle Per Sub-Cluster | Cycle Pattern | Location At Peak |
|---|---|---|---|---|---|---|---|---|---|---|
| 1 | 0 | 176 | 205 | 176 | Yes | Yes | | 1 | | |
| 2 | 176 | 360 | −390 | 184 | Yes | Yes | | 2 | | |
| 3 | 360 | 552 | 480 | 192 | Yes | Yes | | 3 | 480 | |
| 4 | 552 | 664 | −1420 | 112 | Yes | Yes | | 4 | −1420 | 612 |
| 5 | 664 | 808 | 880 | 144 | Yes | Yes | | 5 | −880 | |
| 6 | 808 | 896 | −840 | 88 | Yes | Yes | | 6 | | |
| 7 | 896 | 1016 | 440 | 120 | Yes | Yes | | 7 | 440 | |
| 8 | 1016 | 1128 | −1040 | 112 | Yes | Yes | | 8 | −1040 | 1080 |
| 9 | 1128 | 1296 | 660 | 168 | Yes | Yes | | 9 | 660 | |
| 10 | 1296 | 1496 | 440 | 200 | Yes | Yes | | 10 | | |
| 11 | 1496 | 1616 | 180 | 120 | Yes | Yes | 1616 | 11 | | |
| 12 | 1616 | 1712 | −120 | 96 | No | | | | | |
| 13 | 1712 | 1816 | 60 | 104 | No | | | | | |
| 14 | 1816 | 1960 | −140 | 144 | No | | | | | |
| 15 | 1960 | 2040 | −200 | 80 | Yes | No *** | | | | |
| 16 | 2040 | 2088 | 160 | 48 | No | | | | | |
| 17 | 2088 | 2112 | −20 | 24 | No | | | | | |
| 18 | 2112 | 2136 | 40 | 24 | No | | | | | |
| 19 | 2136 | 2152 | 0 | 16 | No | | | | | |
| 20 | 2152 | 2240 | 180 | 88 | Yes | No *** | | | | |
| 21 | 2240 | 2248 | 0 | 8 | No | | | | | |
| 22 | 2248 | 2400 | −340 | 152 | Yes | No *** | | | | |
| 23 | 2400 | 2640 | 140 | 240 | No | | | | | |
| 24 | 2640 | 2696 | −60 | 56 | No | | 1200 | | | |
| 25 | 2696 | 2792 | −960 | 96 | Yes | Yes | | 1 | −960 | |
| 26 | 2792 | 2888 | 1240 | 96 | Yes | Yes | | 2 | 1240 | 2824 |
| 27 | 2888 | 3024 | −660 | 136 | Yes | Yes | | 3 | −660 | |
| 28 | 3024 | 3152 | 500 | 128 | Yes | Yes | | 4 | | |
| 29 | 3152 | 3280 | −320 | 128 | Yes | Yes | 488 | 5 | | |
| 30 | 3280 | 3448 | 100 | 168 | No | | | | | |
| 31 | 3448 | 3728 | −60 | 280 | No | | | | | |
| 32 | 3728 | 3836 | 0 | 108 | No | | | | | |
| 33 | 3836 | 3880 | 40 | 44 | No | | | | | |
| 34 | 3880 | 3896 | 0 | 16 | No | | | | | |

TABLE 1-continued

Analysis to determine the number of syllables & duration

| Sub Cycle Count | From Mem Loc | To Mem Loc | Peak Value | Duration | Above Threshold 1st pass | 2nd pass | Total Duration | No. of Sub cycle Per Sub-Cluster | Cycle Pattern | Location At Peak |
|---|---|---|---|---|---|---|---|---|---|---|
| 35 | 3896 | 3960 | −80 | 64 | No | | | | | |
| 36 | 3960 | 4068 | 0 | 108 | No | | | | | |
| 37 | 4068 | 4160 | 80 | 92 | No | | | | | |
| 38 | 4160 | 4188 | 0 | 28 | No | | | | | |
| 39 | 4188 | 4264 | −40 | 76 | No | | | | | |
| 40 | 4264 | 4272 | 0 | 8 | No | | | | | |
| 41 | 4272 | 4352 | 40 | 80 | No | | | | | |
| 42 | 4352 | 4360 | 0 | 8 | No | | | | | |
| 43 | 4360 | 4448 | −40 | 88 | No | | | | | |
| 44 | 4448 | 4504 | 0 | 56 | No | | | | | |
| 45 | 4504 | 4680 | −60 | 176 | No | | | | | |
| 46 | 4680 | 4688 | 0 | 8 | No | | | | | |
| 47 | 4688 | 4792 | 50 | 104 | No | | | | | |
| 48 | 4792 | 4800 | 0 | 8 | No | | | | | |
| 49 | 4800 | 5040 | −80 | 240 | No | | | | | |
| 50 | 5040 | 5120 | 20 | 80 | No | | | | | |
| 51 | 5120 | 5168 | 0 | 48 | No | | | | | |
| 52 | 5168 | 5320 | 60 | 152 | No | | | | | |
| 53 | 5320 | 5480 | −140 | 160 | No | | | | | |
| 54 | 5480 | 5520 | 40 | 40 | No | | | | | |
| 55 | 5520 | 5628 | −60 | 108 | No | | | | | |
| 56 | 5628 | 5804 | 160 | 176 | No | | | | | |
| 57 | 5804 | 6048 | −50 | 244 | No | | | | | |
| 58 | 6048 | 6084 | 0 | 36 | No | | | | | |
| 59 | 6084 | 6240 | −140 | 156 | No | | 2960 | | | 2960 |
| 60 | 6240 | 6440 | 260 | 200 | Yes | Yes - *** | | 1 | | |
| 61 | 6440 | 6444 | 0 | 4 | No | | | 0 | | |
| 62 | 6444 | 6656 | −400 | 212 | Yes | Yes | | 2 | | |
| 63 | 6656 | 6872 | 660 | 216 | Yes | Yes | | 3 | 660 | |
| 64 | 6872 | 7008 | −1660 | 136 | Yes | Yes | | 4 | −1660 | 6944 |
| 65 | 7008 | 7184 | 980 | 176 | Yes | Yes | | 5 | 980 | |
| 66 | 7184 | 7280 | −940 | 96 | Yes | Yes | | 6 | | |
| 67 | 7280 | 7424 | 500 | 144 | Yes | Yes | | 7 | 500 | |
| 68 | 7424 | 7552 | −1120 | 128 | Yes | Yes | | 8 | −1120 | 7488 |
| 69 | 7552 | 7744 | 780 | 192 | Yes | Yes | | 9 | 780 | |
| 70 | 7744 | 7984 | −500 | 240 | Yes | Yes | | 10 | | |
| 71 | 7984 | 8132 | 260 | 148 | Yes | Yes | 1892 | 11 | | |
| 72 | 8132 | 8136 | 0 | 4 | No | | | | | |
| 73 | 8136 | 8220 | −80 | 84 | No | | | | | |
| 74 | 8220 | 8944 | 80 | 724 | No | | | | | |
| 75 | 8944 | 9024 | −760 | 80 | Yes | Yes | 892 | 1 | −760 | |
| 76 | 9024 | 9112 | 1200 | 88 | Yes | Yes | | 2 | 1200 | 9056 |
| 77 | 9112 | 9240 | −840 | 128 | Yes | Yes | | 3 | −840 | |
| 78 | 9240 | 9376 | 600 | 136 | Yes | Yes | | 4 | | |
| 79 | 9376 | 9552 | −240 | 176 | Yes | Yes | 528 | 5 | | |
| 80 | 9552 | 9680 | 130 | 128 | No | | | | | |
| 81 | 9680 | 9748 | 40 | 68 | No | | | | | |
| 82 | 9748 | 9764 | 20 | 16 | No | | | | | |
| 83 | 9764 | 9884 | −200 | 120 | Yes | No - *** | | | | |
| 84 | 9884 | 9956 | 60 | 72 | No | | | | | |
| 85 | 9956 | 9988 | −20 | 32 | No | | | | | |
| 86 | 9988 | 10032 | −30 | 44 | No | | | | | |
| 87 | 10032 | 10148 | −100 | 116 | No | | | | | |
| 88 | 10148 | 10288 | 80 | 140 | No | | | | | |
| 89 | 10288 | 10396 | −60 | 108 | No | | | | | |
| 90 | 10396 | 10540 | 100 | 144 | No | | | | | |
| 91 | 10540 | 10664 | −160 | 124 | No | | | | | |
| 92 | 10664 | 10752 | 60 | 88 | No | | | | | |
| 93 | 10752 | 10888 | −80 | 136 | No | | | | | |
| 94 | 10888 | 10960 | 45 | 72 | No | | | | | |
| 95 | 10960 | 11008 | −20 | 48 | No | | | | | |
| 96 | 11008 | 11088 | −40 | 80 | No | | | | | |
| 97 | 11088 | 11112 | 5 | 24 | No | | | | | |
| 98 | 11112 | 11160 | 25 | 48 | No | | | | | |
| 99 | 11160 | 11184 | −20 | 24 | No | | | | | |
| 100 | 11184 | 11248 | 40 | 64 | No | | | | | |
| 101 | 11248 | 11408 | −200 | 160 | Yes | No - *** | | | | |
| 102 | 11408 | 11520 | 100 | 112 | No | | | | | |
| 103 | 11520 | 11660 | −60 | 140 | No | | | | | |
| 104 | 11660 | 11680 | 0 | 20 | No | | | | | |
| 105 | 11680 | 11820 | −100 | 140 | No | | | | | |

TABLE 1-continued

Analysis to determine the number of syllables & duration

| Sub Cycle Count | From Mem Loc | To Mem Loc | Peak Value | Duration | Above Threshold 1st pass | 2nd pass | Total Duration | No. of Sub cycle Per Sub- Cluster | Cycle Pattern | Location At Peak |
|---|---|---|---|---|---|---|---|---|---|---|
| 106 | 11820 | 11988 | 55 | 168 | No | | | | | |
| 107 | 11988 | 12176 | −80 | 188 | No | | | | | |
| 108 | 12176 | 12320 | 0 | 144 | No | | 2768 | | | |
| 109 | 12320 | 12500 | 204 | 180 | Yes | Yes | | 0 | | |
| 110 | 12500 | 12684 | −400 | 184 | Yes | Yes | | 0 | | |
| 111 | 12684 | 12876 | 500 | 192 | Yes | Yes | | | | |

The data obtained as described above is stored in memory and is then examined to identify those subcycle units which will be assumed to be the result of noise and each of these subcycle units is treated during subsequent analysis as having a value of zero. This operation is performed in two phases.

In the first phase, each subcycle unit having a peak value which is less than 10% of the maximum allowed signal value will be marked to be assigned a value of zero. For example, if the A/D converter used to produce the digital sample values is capable of converting voltages between −6V and +6V into digital values which can be represented in decimal form as extending between −2047 and +2047, the detected signal is amplified, prior to sampling, to a level such that the maximum amplitude excursion of the signal to be sampled is between −5V and +5V, which corresponds to digital values expressed in decimal form as −1706 and +1706. In this case, each stored value whose decimal representation is between +170 and −170 will be marked to be treated as having a value of zero. This is indicated, in the database represented by Table 1, by storing "No" in the column labeled "1st pass". For those subcycle units having a stored value with an absolute value greater than 170, the notation "yes" is stored in the column labeled "1st pass".

Then, in a second phase, all of the samples which have not been marked to be treated as having a value of zero are reexamined and each one of these samples which is bordered on both sides by sample values which have been marked for conversion to zero at more than 20 consecutive memory addresses, corresponding to a duration of 5 milliseconds, are also considered to be noise signals and are marked to be treated as having a value of zero by placing the notation "No" in the column labeled "2nd pass".

The result of the operations performed in these two phases, or passes, for the signal shown in FIG. 1 is included in Table 1.

Then, the subcycle units having peak values above the threshold are grouped into subclusters. Each subcluster is composed of consecutive or nearly consecutive subcycle units each containing a peak with an absolute value greater than 170. Two subcycle units having absolute peak values greater than 170 will be considered to belong to the same subcluster if they are separated from one another by no more than 20 memory addresses containing zero values after conversion.

In the next step, successive subclusters are examined to identify the succession of initially stored samples which correspond to one complete heartbeat, which is generally considered to correspond to a heart pulsation containing one complete systole and diastole. According to the present invention, this is achieved by first determining the number of subclusters in a single heartbeat, followed by a determination of the duration of one heartbeat.

In order to identify the number of subclusters in a single heartbeat, the stored subcycle unit data shown in Table 1 is scanned, starting from subcycle unit 1, and each successive subcycle unit having a peak absolute value greater than 170 is considered to be part of a subcluster. In addition, as noted above, if two successive subcycle units having a peak absolute value greater than 170 are separated from one another by a subcycle unit initially containing only sample values which are less than 170 and having a duration of fewer than 40 memory locations (20 memory addresses), the subcycle units which are separated from one another by the latter subcycle unit are considered to belong to the same cluster. However, in this case, the intervening subcycle unit is not counted as one of the subcycle units of the subcluster. For example, in Table 1, subcycle unit 60 has a peak value of 260, subcycle unit 61 has a zero value and a duration of four memory locations, and subcycle unit 62 has a peak value of −400. Therefore, subcycle units 60 and 62 belong to the same subcluster and subcycle unit 61 is not counted as part of that subcluster.

After the end of each subcluster has been identified, the duration of that subcluster, represented by the number of memory locations encompassed by that subcluster, can be determined and stored in memory, as represented by the values in the column labeled "Total Duration" in Table 1. Similarly, the number of memory locations between the end of one subcluster and the beginning of the next subcluster can be counted and stored in memory, also as in the column labeled "Total Duration".

Furthermore, selected subcycle unit peak values in each subcluster can be stored in memory as shown in the column labeled "Cycle Pattern" in Table 1. The selection of subcycle units whose peak values are to be stored can be based on the number of subcycle units in the associated subcluster. The number of subcycle units in each subcluster is determined by assigning and storing in the database a count number to each subcycle unit in each subcluster and taking the count assigned to the last subcycle unit in each subcluster, as shown in the column labeled "No. Of Subcycle Units per Subcluster". For example, if the number of subcycle units in a subcluster is greater than 8, then the two largest magnitude peak values of the subcycles in that subcluster are selected, whereas if the number of subcycles in a subcluster is 8 or less, only the single largest subcycle unit peak value is selected. The selected peak values are stored in the database, as represented by the column labeled "Cycle Pattern" in Table 1. In the example illustrated in Table 1, each subcluster containing 11 subcycle units has the greatest peak magnitudes at the 4th and 8th subcycle units. The peak values of the subcycle units adjacent each largest peak value in a subcluster can also be stored in memory, as shown in Table 1.

Successive subcycle units between subclusters are also examined and the number of memory locations between successive subclusters is stored in memory. These stored values are shown in the column labeled "Total Duration" in Table 1. For example, subcycle counts 12–24 are located between the first and second subclusters and cover 1200 successive memory locations.

The second subcluster encountered contains subcycle units 25–29 with the largest peak magnitude being in subcycle unit 26. Therefore, the peak values associated with subcycle units 25, 26 and 27 are identified and stored.

The same process continues through the rest of the stored samples, also as indicated in Table 1. For example, after the second subcluster, the third subcluster, the third subcluster begins with subcycle unit 60 which is found to be 2960 memory locations after subcycle unit 29.

Then, characteristics of each subcluster can be compared with those of every other subcluster, based on selected criteria. The first criterion would be the number of subcycle units per subcluster. Specifically, the number of subcycle units in the first subcluster will be compared with the number of subcycle units in each succeeding subcluster and for any succeeding subcluster which has the same number of subcycle units as the first subcluster, ±1, an initial assumption is made that these subclusters are corresponding subclusters of successive heartbeats.

Since it can be assumed that a complete heartbeat contains between two and four subclusters, the first subcluster is initially compared with the third subcluster. In the example shown in FIGS. 1 and 2 and Table 1, the first and third subclusters are found to each consist of 11 subcycle units. Examination of the selected peak values of these subclusters shows that in both the two largest peak values are in the fourth and eighth subcycle units and that each largest peak value in the first subcluster is within 20% of the corresponding largest peak value in the third subcluster, a 20% differential being a suitable criterion for determining the two subclusters are corresponding subclusters of successive heartbeats.

When the comparison of the first and third subclusters produces the above-described results, a similar comparison is made of the corresponding features of the second and fourth subclusters. In the instant example, this comparison reveals that these two subclusters both consist of five subcycle units with maximum peak values of 1240 and 1200, respectively.

If this determination shows that the second and fourth subclusters have comparable patterns, it can be concluded that a single heartbeat consists of two subclusters, or is a two syllable heartbeat.

If desired, a further confirmation can be achieved by comparing the time durations between successive subclusters identified as being associated with a first heartbeat and successive subclusters determined to be corresponding subclusters associated with the next succeeding heartbeat. These time intervals represent "silent periods" containing initially stored signals that were judged to represent noise. If corresponding silent periods are found to have comparable durations, it can be further confirmed that the number of subclusters in a single heartbeat has been identified.

For example, in the specific case illustrated in Table 1, the silent periods between successive subclusters have durations of 1200, 2960, 892 and 2768 memory locations, respectively. Using experimentally derived criteria, such as, for example, the percentage difference between respective silent periods, it would be concluded that the first and third silent periods correspond to one another, as do the second and fourth silent periods. This allows confirmation of the conclusion that the stored heartbeat sound is a two-syllable heartbeat.

The next step is to determine the heartbeat period, i.e., the inverse of heartbeat rate, based on the stored data identifying the number of memory locations associated with each subcluster and each silent period, as shown in the "Total Duration" column of Table 1. The total period of the first heartbeat, represented by the durations of the first and second subclusters and the first and second silent periods, is 6240 memory locations, or 780 msec. The total duration of the second heartbeat is 760 msec. The difference between these periods is 20 msec. If the two time periods differ by no more than 10%, it will be assumed that they relate to complete heartbeats.

It should be mentioned that to date, sound pattern recordings from over 200 patients with different heart conditions have been sampled and analyzed. Every one of those sound patterns could be successfully identified by the procedure described above.

As the next step, it is necessary to select a starting memory location for reproduction of a heartbeat. For example, this can be the memory location associated with the midpoint of the longer quiet period. For this purpose, it is merely necessary to select the memory location which is midway between the first memory location and the last memory location associated with the longer quiet period.

Figure 2:
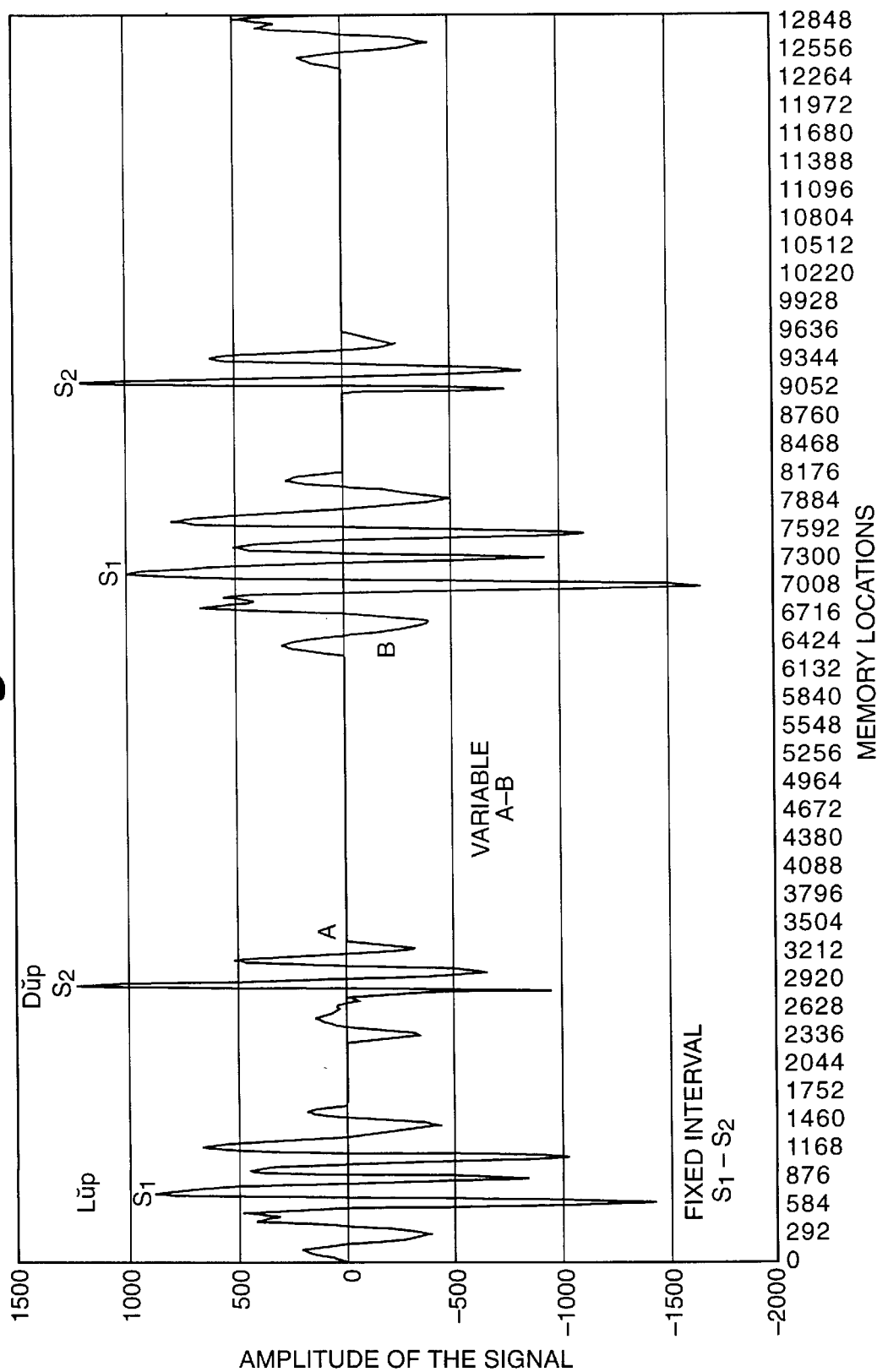

In the example shown in FIGS. 1 and 2 and Table 1, the longer quiet period for the first heartbeat starts at memory location 3280 and ends at memory location 6240. Therefore, the starting location is (6240−3280)/2+3280=4760.

Then, the ending memory location for reproduction of a heartbeat is determined simply by adding the total number of memory locations associated with the previously calculated heartbeat period, which is 6240, to the starting memory location, 4760. Thus, the ending memory location is 11000.

The procedures described above can be controlled by a program which can be easily written by any programmer of at least ordinary skill in the programming art.

Then, the samples which are contained in the memory locations between the starting memory location and the ending memory location can be supplied, at a rate equal to the original sampling rate, to a digital-analog converter. This latter step will be performed repetitively at a rate determined by the user, preferably by acting on a manual control element.

The process for reproducing a heartbeat at a selected repetition rate can be carried out under control of a simple program, such as the following program, which is written in Pseudo Code.

Step 1. Set Memory location 4760 to a label "Start".
Step 2. Set Memory location 11000 to a label "End".
Step 3. Do While CURRENT_LOCATION (From Start to End in Steps of 2).
Step 4. Read CURRENT_LOCATION and CURRENT_LOCATION+1.
Step 5. Write contents of CURRENT_LOCATION and CURRENT_LOCATION+1 to D/A converter Buffer.
Step 6. Increment CURRENT_LOCATION by 2.
Step 7. Repeat steps 4, 5 and 6 until CURRENT_LOCATION is equal to End.

Step 8. Wait for requested time delay, and repeat Steps 3 to 7.

Thus, the present invention allows a single heartbeat to be reproduced repeatedly at a repetition rate selected by the user, without altering the frequency components in the heartbeat itself, so that the original heartbeat is faithfully reproduced at any desired repetition rate for diagnostic or teaching purposes.

Figure 3:
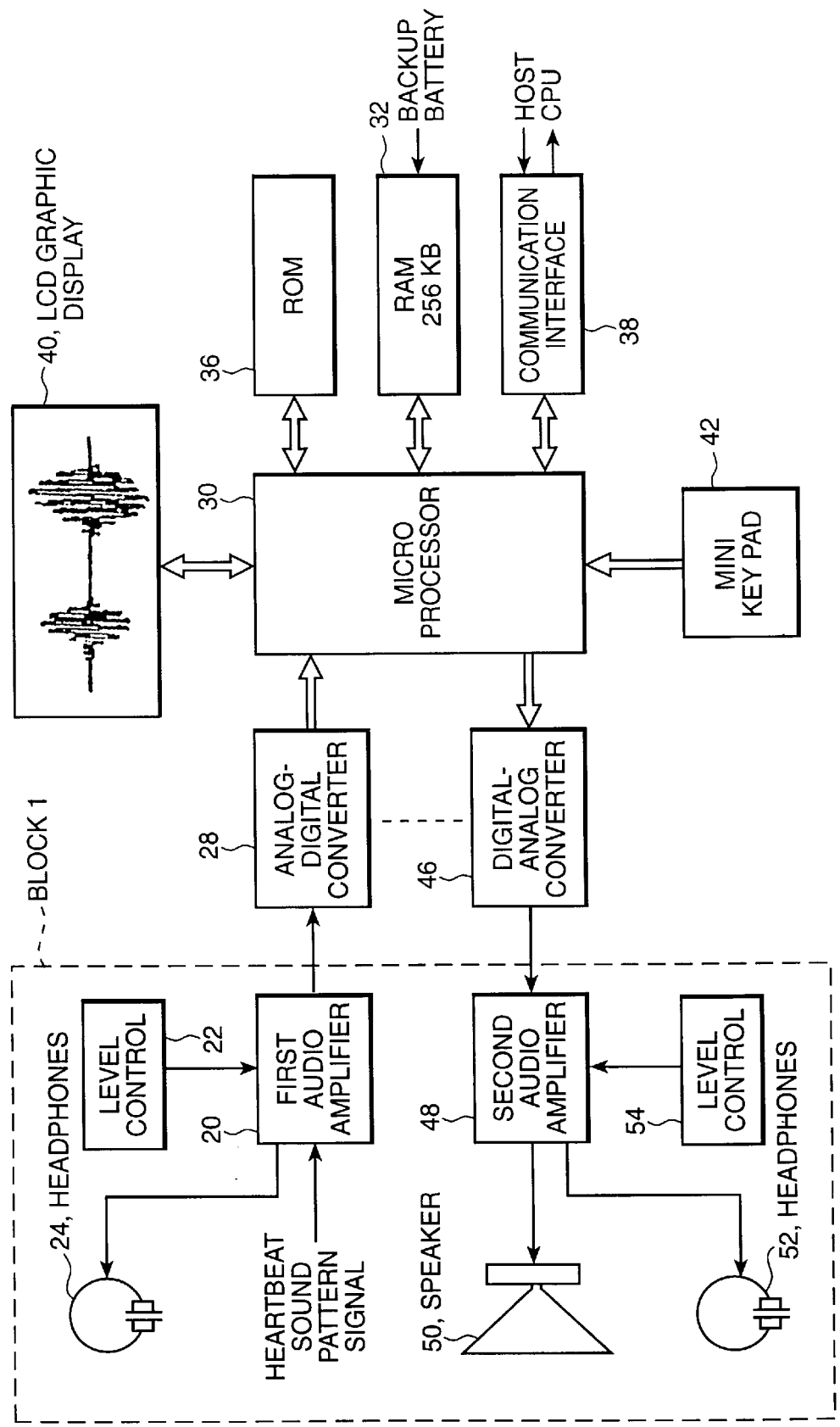
FIG. 3 is a block diagram of one preferred embodiment of apparatus according to the present invention.

FIG. 3 is a block diagram of one exemplary but nonlimiting embodiment of a system according to the present invention.

This system includes a first block, identified as BLOCK-1, containing components which will be coupled in any suitable manner to any known electronic stethoscope having a microphone which produces an electrical output. The output from the microphone is supplied to a signal input of a first audio amplifier 20 having an adjustable amplification determined by the setting of a level control 22. Heartbeat sound pattern signals supplied to amplifier 20 are delivered to a first output which can be connected to a first set of headphones 24. Output signals from amplifier 20 are additionally supplied to an analog-digital converter 28 which samples the output signal from amplifier 20 and derives a digital value for each sample, as described earlier herein. These digital sample value representations are conveyed under control of a microprocessor or CPU 30 to a RAM 32 which stores the signals in successive memory locations, as also described earlier herein.

Operation of microprocessor 30 is controlled by a program, which may be a firmware program contained in a ROM 36. In addition, microprocessor 30 may communicate with a host CPU via a communication interface 38.

The digital system may additionally be provided, as desired, with a display 40 and an input keypad 42, both connected to microprocessor 30. After the range of memory locations containing samples which are to be reproduced has been determined, these locations are read out, at the same rate as the rate employed in the sampling operation, to a digital-analog converter 46 which produces an analog output signal that is supplied to the signal input of a second audio amplifier 48. Audio amplifier 48 may have a plurality of outputs connected, for example, to a speaker 50 and/or a second pair of headphones 52. The gain of amplifier 48 may be controlled by an appropriate level control component 54.

All of the components illustrated in FIG. 3 may be constituted by conventional, commercially available devices.

The delay between repetitions of one stored heartbeat, or heart pulsation cycle, can be controlled by inputting the desired repetition rate via keypad 42.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A method for audibly reproducing a heartbeat at a user-selected repetition rate, said method comprising:
   detecting sound patterns produced by successive heartbeats and storing a representation of the sound patterns over a time period that encompasses at least one heartbeat cycle;
   analyzing the stored representation to determine the duration of one heartbeat cycle;
   audibly reproducing a portion of the stored representation extending over one heartbeat cycle such that the audibly reproduced portion extends over a time period substantially equal to the duration of one heartbeat cycle; and
   repeating the step of audibly reproducing at the user-selected repetition rate, which repetition rate is lower than the heartbeat rate of the heartbeats whose sound patterns are detected.

2. The method according to claim 1 wherein the detected heart sound patterns are composed of a plurality of oscillation subclusters, each subcluster containing a plurality of oscillation subcycles, successive oscillation subclusters being spaced apart by respective time periods; and said step of analyzing comprises:
   determining the number of subcycles in each subcluster; and
   identifying successive subclusters having substantially the same number of subcycles as subclusters of successive heartbeats.

3. The method according to claim 2, wherein each oscillation subcycle has a peak value and said step of analyzing further comprises:
   identifying that subcycle in each subcluster which has the maximum peak value; and
   comparing the magnitudes of the maximum peak values in successive subclusters which were identified as having substantially the same number of subcycles.

4. The method according to claim 3 wherein said step of analyzing is performed by considering only subcycles having a peak value above a given threshold and having a given time proximity to at least one other subcycle having a peak value above the given threshold.

5. The method according to claim 4 further comprising varying the user-selected repetition rate.

6. The method according to claim 5 wherein said steps of detecting and storing comprise sampling the heart sound patterns at a selected sampling rate, producing a digital representation of the amplitude of each heart sound sample, and storing each digital representation at a respective address in a memory.

7. Apparatus for audibly reproducing a sound pattern produced by a heartbeat at a user-selected repetition rate, said apparatus comprising:
   means for detecting the audible sound patterns produced by heartbeats and storing a representation of such sound patterns occurring over a period of time that encompasses one heartbeat cycle;
   means for analyzing the stored representation to determine the duration of one heartbeat cycle;
   means for audibly and repeatedly reproducing a portion of the stored representation extending over one heartbeat cycle such that each repetition of the audibly reproduced portion extends over a time period substantially equal to the duration of one heartbeat cycle; and
   means for selecting the repetition rate at which the portion of the stored representation is repeatedly produced.

8. The apparatus according to claim 7 wherein the detected heart sound patterns are composed of a plurality of oscillation subclusters, each subcluster containing a plurality of oscillation subcycles, successive oscillation subclusters being spaced apart by respective time periods; and said means for analyzing comprises:
   means for determining the number of subcycles in each subcluster; and means for identifying successive subclusters having substantially the same number of subcycles as subclusters of successive heartbeats.

9. The apparatus according to claim 7, wherein each oscillation subcycle has a peak value and said means for analyzing further comprises:

means for identifying that subcycle in each subcluster which has the maximum peak value; and means for comparing the magnitudes of the maximum peak values in successive subclusters which were identified as having substantially the same number of subcycles.

10. The apparatus according to claim 9 wherein said means for analyzing is performed by considering only subcycles having a peak value above a given threshold and having a given time proximity to at least one other subcycle having a peak value above the given threshold.

11. The apparatus according to claim 7 wherein said means for detecting and storing comprise means for sampling the heart sound patterns at a selected sampling rate, means for producing a digital representation of the amplitude of each heart sound sample, and means for storing each digital representation at a respective address in a memory.

* * * * *